United States Patent
Chao et al.

(10) Patent No.: US 6,604,853 B2
(45) Date of Patent: Aug. 12, 2003

(54) ACCELERATED THERMAL STRESS CYCLE TEST

(75) Inventors: Ying-Chen Chao, Dung Chiu (TW); Wi William Lee, Tainan (TW); Sen-Shan Yang, Tainan (TW); Keng-Hui Liao, Peng-Tung County (TW)

(73) Assignee: Taiwan Semiconductor Manufacturing Co., Ltd, Hsin Chu (TW)

( * ) Notice: Subject to any disclaimer, the term of this patent is extended or adjusted under 35 U.S.C. 154(b) by 0 days.

(21) Appl. No.: 09/976,995

(22) Filed: Oct. 11, 2001

(65) Prior Publication Data

US 2003/0072350 A1 Apr. 17, 2003

(51) Int. Cl.⁷ .................... G01N 17/00; G01N 25/00; G01R 31/26
(52) U.S. Cl. ...................... 374/57; 374/5; 73/865.6; 324/760
(58) Field of Search ................ 374/57, 5, 47, 374/45; 324/760, 765, 537; 427/124; 438/14, 18; 165/201, 267, 65; 73/865.6; 414/935

(56) References Cited

U.S. PATENT DOCUMENTS

| | | | | | |
|---|---|---|---|---|---|
| 4,951,601 | A | * | 8/1990 | Maydan et al. ............. 414/935 |
| 5,147,136 | A | * | 9/1992 | Hartley et al. ............. 374/57 |
| 5,167,451 | A | * | 12/1992 | Muller et al. .............. 374/57 |
| 5,269,370 | A | * | 12/1993 | Christian et al. ........... 374/57 |
| 5,410,162 | A | * | 4/1995 | Tigelaar et al. ............ 374/57 |
| 5,563,520 | A | * | 10/1996 | Terada ..................... 324/760 |
| 5,636,924 | A | * | 6/1997 | McCracken et al. .......... 374/57 |
| 5,719,495 | A | * | 2/1998 | Moslehi ................... 324/765 |
| 5,980,103 | A | * | 11/1999 | Ikuno et al. ............... 374/57 |
| 6,113,262 | A | * | 9/2000 | Purola et al. .............. 374/57 |
| 6,440,261 | B1 | * | 8/2002 | Tepman et al. ............. 414/935 |
| 6,488,778 | B1 | * | 12/2002 | Ballantine et al. ......... 414/935 |

* cited by examiner

Primary Examiner—Diego Gutierrez
Assistant Examiner—Stanley J. Pruchnic, Jr.
(74) Attorney, Agent, or Firm—Tung & Associates

(57) ABSTRACT

An accelerated thermal stress cycle test which can be conducted in a significantly reduced test time compared to the conventional test is provided. The test is carried out in a cluster of reaction chambers that includes a CVD chamber and a cool-down chamber such that a pre-processed wafer can be heated from room temperature to at least 350° C. in an inert gas in about 2 min., and then cooled down to not higher than 70° C. in a cool-down chamber in less than 30 sec. The heating and cooling steps can be repeated between 3 and 7 times to reveal any defect formation caused by the thermal stress cycle test. Typical defects are metal film peeling from insulating dielectric material layer or void formation.

18 Claims, No Drawings

ACCELERATED THERMAL STRESS CYCLE TEST

FIELD OF THE INVENTION

The present invention generally relates to a reliability test for semiconductor chips and more particularly, relates to an accelerated thermal stress cycle test for semiconductor chips.

BACKGROUND OF THE INVENTION

In semiconductor fabrication technologies, the reliability test conducted on the semiconductor chips fabricated is an important part of the total fabrication process. One of such reliability tests is the thermal stress cycle test or the thermal voiding test.

In a thermal stress cycle test, the stress experienced by a metallic thin film that played a critical role in the stability of fine line interconnects is tested. The thermal stress cycle test can reveal the thermal voiding defect which is a major problem in passivated copper or aluminum metalization, especially when deposited on stiff dielectrics such as sputtered $SiO_2$ or $SiN_x$. Conventionally, metallic films such as copper or aluminum used as interconnections are subjected to many thermal cycles between room temperature and 400° C., during various processes of deposition, lithography and etching. Since the deposition temperatures for the dielectric insulators may exceed 300° C., some but not all of the film stress can be relieved. For instance, commonly used inorganic insulators such as PECVD oxide, APCVD oxide and nitrides are deposited at temperatures in the range between 300° C. and 500° C. When these deposited insulators are cooled down, the rigid insulators restrict the ability of the metal films to relax thermal stresses imposed on them.

It is known that the driving force for the thermal stress problem is the thermal expansion mismatch between the metal films and the insulating dielectric materials that enclose the films and the silicon substrate. It is theorized that thermal stress-induced failure is caused by the confinement of the copper or aluminum lines or films by the dielectric insulators which have thermal expansion coefficients smaller than that of copper or aluminum. Conventionally, a thermal voiding defect or a metal film peeling defect is studied by thermal cycle samples to a high temperature where grain boundary diffusion is rapid and the stress in the film is close to zero. The sample is typically cycled between room temperature and a high temperature, i.e., between 300° C. and 500° C., and examined periodically for signs of void nucleation or growth and for metal film peeling.

Another reliability test that is frequently conducted simultaneously with the thermal stress cycle test is the thermal shock testing. The objective of thermal shock testing is somewhat similar to that for the thermal stress cycle test. However, the thermal shock test provides additional stress since the device is exposed to a sudden change in temperature due to the rapid rate of temperature change. Failure mechanisms which are caused by temperature transients and temperature gradients can be detected by the thermal shock test. The test can be conducted by either a rapid temperature increase, or a rapid temperature decrease, or by cycling through both. The test is normally conducted for a predetermined number of cycles to detect common failure modes which include parametric shifts and catastrophic events. The common failure mechanisms observed may include wirebond cracked, dies lifted and package failure.

Conventionally, the thermal stress cycle test and the thermal shock test are conducted in a furnace for a predetermined number of cycles. Since a furnace has a large volume and therefore requires a long time for heating or cooling, it is not unusual to require three or four hours for conducting a single thermal cycle between room temperature and a high temperature, i.e. between 300° C. and 500° C. When such furnace cycle test is conducted, even at a minimum of three cycles, a total test time of at least 12 hours is required. The conventional thermal cycle/thermal shock test therefore is a time consuming task which cannot be easily conducted in a timely manner.

It is therefore an object of the present invention to provide a thermal stress cycle test method that does not have the drawbacks or shortcomings of the conventional thermal stress cycle test.

It is another object of the present invention to provide a thermal stress cycle test that does not require the use of a conventional furnace for conducting the test.

It is a further object of the present invention to provide a thermal stress cycle test that can be conducted in a significantly shorter time period when compared to a conventional thermal stress cycle test.

It is another further object of the present invention to provide a thermal stress cycle test and a thermal shock test which can be conducted together.

It is still another object of the present invention to provide a thermal stress cycle test in a cluster of test chambers that includes a heating chamber and a cooling chamber.

It is yet another object of the present invention to provide a thermal stress cycle test wherein the test can be conducted with a 85% reduction in the required test time when compared to a conventional thermal stress cycle test.

It is still another further object of the present invention to conduct a thermal stress cycle test in a chemical vapor deposition chamber for heating and in a cool-down chamber for cooling.

SUMMARY OF THE INVENTION

In accordance with the present invention, an accelerated thermal stress cycle test for the reliability testing of semiconductor chips is provided.

In a preferred embodiment, an accelerated thermal stress cycle test can be carried out by the operating steps of providing a cluster of reaction chambers including at least one chemical vapor deposition (CVD) chamber and at least one cool-down chamber; heating a pre-processed wafer by positioning the wafer in the at least one CVD chamber to at least 350° C. in an inert gas environment for at least 2 min.; cooling the pre-processed wafer by moving from the at least one CVD chamber to the at least one cool-down chamber to a temperature not higher than 70° C.; repeating sequentially the heating and cooling step for at least three times; and determining any defect caused by the repeated heating and cooling steps.

In the accelerated thermal stress cycle test, the cluster of reaction chambers may have a LPCVD chamber and a cool-down chamber, the at least one CVD chamber may be a single wafer LPCVD chamber that includes heating lamps, the at least one CVD chamber is a single wafer LPCVD chamber that includes heating means capable of heating a wafer from 23° C. to 350° C. within 2 min. The at least one CVD chamber is a single wafer LPCVD chamber that includes heating means for heating a wafer from 20° C. to 350° C. within 2 min. in an inert gas environment, such as in $N_2$, He or Ar. The test method may further include the step of moving the pre-processed wafer from the at least one CVD chamber to the at least one cool-down chamber by a robot blade. The method may further include the step of cooling down the pre-processed wafer from at least 350° C. to not higher than 70° C. in a time period of not less than 30 sec. The method may further include the step of repeating sequentially the heating and cooling steps between 3 and 10 times, or preferably between 4 and 7 times.

The present invention is further directed to a thermal stress cycle test that can be carried out by the operating steps of providing a heating chamber and a cooling chamber positioned juxtaposed to each other; positioning a pre-processed wafer in the heating chamber and heating the pre-processed wafer from 23° C. to at least 350° C. in less than 2 min.; positioning the pre-processed wafer in the cooling chamber and cooling the wafer from 350° C. to not higher than 70° C. in less than 30 sec.; repeating sequentially the heating and cooling steps for at least 3 times; and determining any defect formed on the pre-processed wafer.

The method for thermal stress cycle test may further include the step of transporting the pre-processed wafer from the heating chamber to the cooling chamber by a robot blade. The method may further include the step of providing a cluster of reaction chambers that contains the heating chamber and the cooling chamber, or the step of providing the heating chamber in a single wafer LPCVD chamber, or the step of providing the heating chamber equipped with heating lamps. The method may further include the step of flowing an inert gas selected from the group consisting of $N_2$, He and Ar into the heating and cooling chambers, or the step of flowing $N_2$ into the heating chamber during the heating cycle. The method may further include the step of repeating sequentially the heating and cooling steps for at least 7 times, or preferably between 7 times and 10 times. The method may further include the step of determining any peeling of a copper layer from a dielectric material layer.

DETAILED DESCRIPTION OF THE PREFERRED EMBODIMENT

The present invention discloses a reliability test method of an accelerated thermal stress cycle test, or an accelerated thermal stress cycle test/thermal shock test for the reliability testing of semiconductor wafers, or the semiconductor chips on the wafers.

The present invention accelerated thermal stress cycle test, when compared to a conventional thermal stress cycle test that is conducted in a traditional furnace, can save the test time by as much as 85%. The savings in test time is made possible by utilizing a reaction chamber that can be rapidly heated to a high temperature of at least 350° C. within a short time period, i.e., within 2 min., and cooling the heated wafer to room temperature in a cool-down chamber within a short time period of about 30 sec. The rapid heating process is made possible by conducting the test in a chemical vapor deposition chamber, such as a low pressure CVD chamber that is equipped with heating lamps capable of rapidly heating a wafer from room temperature to about 350° C. in 2 min. The cool-down chamber is positioned nearby the heating chamber such that the wafer can be transferred over rapidly by a robot blade for conducting the rapid cool-down process in the cool-down chamber, i.e. from 350° C. to not higher than 70° C. in about 30 sec.

The present invention novel accelerated thermal stress cycle test can be advantageously conducted in a cluster of reaction chambers such as one that contains at least one CVD chamber and at least one cool-down chamber. The cool-down process can be conducted in a large flow of inert gas of $N_2$, He or Ar. The heating process should also be conducted in an inert gas environment that is filled with $N_2$, He or Ar to avoid any oxidation process or other chemical reactions.

One example of the present invention novel accelerated thermal stress cycle test is conducted in a cluster of reaction chambers that includes at least one chemical vapor deposition chamber, i.e., a single-wafer LPCVD chamber, and at least one cool-down chamber juxtaposed to the CVD chamber. After the heating process, the wafer can be rapidly transported to the cool-down chamber by a robot transfer blade for the thermal shock test. A pre-processed wafer that has a metal film layer of copper or aluminum deposited on insulating dielectric layers is then positioned in the CVD chamber and heated to a temperature of at least 350° C., and preferably to a temperature of at least 400° C. in an inert gas environment such as nitrogen for at least 2 min. After the heating time is reached, the heated wafer is rapidly transported from the heating chamber to the cooling chamber that is positioned nearby such that the wafer can be rapidly cooled in a flow of inert gas to a temperature not higher than 70° C., and preferably to a temperature not higher than 30° C. The heating and the cooling steps are then repeated sequentially for at least 3 times or for between 3 times and 10 times, and more preferably for about 7 times. The pre-processed wafer is then examined under a microscope to detect any defects, such as film peeling or void formation under the film that is caused by the thermal stress or by the coefficient of thermal expansion mismatch.

To achieve the thermal shock effect on the pre-processed wafer, when the heated wafer is transferred to the cool-down chamber, the wafer should be cooled from at least 350° C. to a temperature not higher than 70° C. within a short time period of about 30 sec.

The present invention novel process for an accelerated thermal stress cycle test can further be conducted by first providing a heating chamber and a cooling chamber that are positioned juxtaposed to each other, then placing a pre-processed wafer in a heating chamber and heating the wafer from 23° C. to at least 350° C. in less than 2 min., then transporting the pre-processed wafer to the cooling chamber for cooling the wafer from 350° C. to not higher than 70° C. in less than 30 sec., repeating sequentially the heating and cooling steps for at least 3 times, or preferably between 3 and 7 times, and determining any defect formed on the pre-processed wafer such as metal film peeling or void formation. The cooling processed can be most efficiently carried out by exposing the wafer to a rapid flow of low temperature inert gas.

While the present invention has been described in an illustrative manner, it should be understood that the terminology used is intended to be in a nature of words of description rather than of limitation.

Furthermore, while the present invention has been described in terms of a preferred embodiment, it is to be appreciated that those skilled in the art will readily apply these teachings to other possible variations of the inventions.

The embodiment of the invention in which an exclusive property or privilege is claimed are defined as follows.

What is claimed is:

1. An accelerated thermal stress cycle test comprising the steps of:

providing a cluster of reaction chambers including at least one chemical vapor deposition (CVD) chamber and at least one cool-down chamber;

heating a pre-processed wafer to at least 350° C. in less than 2 minutes by positioning said wafer in one of said at least one CVD chambers in an inert gas;

cooling said pre-processed wafer to a temperature not higher than 70° C. in less than 30 seconds by moving said wafer from said at least one CVD chamber to one of said at least one cool-down chambers;

repeating sequentially said heating and cooling steps for at least three times; and determining any defect caused by said repeated heating and cooling steps.

2. An accelerated thermal stress cycle test according to claim 1, wherein said cluster of reaction chambers having a LPCVD chamber and a cool-down chamber.

3. An accelerated thermal stress cycle test according to claim 1, wherein said at least one CVD chamber is a single wafer LPCVD chamber comprising heating lamps.

4. An accelerated thermal stress cycle test according to claim 1, wherein said at least one CVD chamber is a single wafer LPCVD chamber comprising heating means for heating a wafer from 23° C. to 350° C. within 2 minutes.

5. An accelerated thermal stress cycle test according to claim 1, wherein said at least one CVD chamber is a single wafer LPCVD chamber comprising heat means for heating a wafer from 23° C. to 350° C. within 2 minutes in an inert gas environment.

6. An accelerated thermal stress cycle test according to claim 1, wherein said at least one CVD chamber is a single wafer LPCVD chamber comprising heating means for heating a wafer from 23° C. to 350° C. within 2 minutes in an inert gas environment on $N_2$, He or Ar.

7. An accelerated thermal stress cycle test according to claim 1 further comprising the step of moving said pre-processed wafer from one of said at least one CVD chamber to one of said at least on cool-down chamber by a robot blade.

8. An accelerated thermal stress cycle test according to claim 1 further comprising the step of repeating sequentially said heating and cooling steps between 3 and 10 times.

9. An accelerated thermal stress cycle test according to claim 1, further comprising the step of repeating sequentially said heating and cooling steps for 7 times.

10. A thermal stress cycle test comprising the steps of:

providing a heating chamber and a cooling chamber positioned juxtaposed to each other, said heating chamber being a single-wafer LPCVD chamber;

positioning a preprocessed wafer in said heating chamber and heating said pre-processed wafer from 23° C. to at least 350° C. in less than 2 minutes;

positioning said pre-processed wafer in said cooling chamber and cooling said pre-processed wafer from 350° C. to not higher than 70° C. in less than 30 seconds;

repeating sequentially said heating and cooling steps for at least 3 times; and determining any defect formed on said pre-processed wafer.

11. A thermal stress cycle test according to claim 10 further comprising the step of transporting said pre-processed wafer from said heating chamber to said cooling chamber by a robot blade.

12. A thermal stress cycle test according to claim 10 further comprising the step of providing a cluster of reaction chambers that includes said heating chamber and said cooling chamber.

13. A thermal stress cycle test according to claim 10 further comprising the step of providing said heating chamber in a chamber equipped with heating lamps.

14. A thermal stress cycle test according to claim 10 further comprising the step of flowing an inert gas selected from the group consisting of $N_2$, He and Ar into said heating and cooling chambers.

15. A thermal stress cycle test according to claim 10 further comprising the step of flowing $N_2$ into said heating chamber during the heating cycle.

16. A thermal stress cycle test according to claim 10 further comprising the step of repeating sequentially said heating and cooling steps for at least 7 times.

17. A thermal stress cycle test according to claim 10 further comprising the step of determining any peeling of a Cu layer from a dielectric material layer.

18. A thermal stress cycle test according to claim 10 further comprising the step of repeating sequentially said heating and cooling steps between 3 times and 10 times.

* * * * *